US00PP31501P2

(12) United States Plant Patent
Bean et al.

(10) Patent No.: US PP31,501 P2
(45) Date of Patent: Feb. 25, 2020

(54) ***PLECTRANTHUS* PLANT NAMED 'DE WET F'**

(50) Latin Name: ***Plectranthus* hybrid**
Varietal Denomination: De Wet F

(71) Applicant: Charles Andrew de Wet, Johannesburg (ZA)

(72) Inventors: Quinton Bean, Johannesburg (ZA); Charles Andrew de Wet, Johannesburg (ZA)

(73) Assignee: Charles Andrew de Wet, Johannesburg (ZA)

( * ) Notice: Subject to any disclaimer, the term of this patent is extended or adjusted under 35 U.S.C. 154(b) by 0 days.

(21) Appl. No.: 16/501,300

(22) Filed: Mar. 21, 2019

(51) Int. Cl.
*A01H 5/02* (2018.01)
*A01H 6/50* (2018.01)

(52) U.S. Cl.
USPC ..... Plt./469

(58) Field of Classification Search
USPC ..... Plt./263.1, 469
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Plectranthus* plant, 'De Wet F' that is characterized by its large purple flowers, its floriferous blooming habit, and its well-branched plant habit.

2 Drawing Sheets

Botanical classification: *Plectranthus* hybrid.
Variety denomination: 'De Wet F'.

BACKGROUND OF THE INVENTION

The present invention relates to a new and distinct cultivar of *Plectranthus* of hybrid origin and will be referred to hereafter by its cultivar name, 'De Wet F'. 'De Wet F' is grown as a perennial landscape plant.

The new *Plectranthus* resulted from a breeding program conducted by the Inventors in Linbro Park, Johannesburg, South Africa. The goals of the breeding program were to develop new cultivars of *Plectranthus* with abundant large flowers on plants with good branching and strong and vigorous growth habits. The Inventors made crosses in March of 2015 between unnamed proprietary plants (not patented) of *Plectranthus* in the Inventor's breeding program as both the female parent and male parent. The exact parent plants are unknown as seeds were pooled from the crosses. 'De Wet F' was selected as a single unique plant in November 2015 from the resulting seedlings of the above crosses.

Asexual propagation of the new cultivar was first accomplished by one of the Inventors by stem cuttings in December of 2015 in Linbro Park, Johannesburg, South Africa. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'De Wet F' as a unique cultivar of *Plectranthus*.

1. 'De Wet F' exhibits large purple flowers.
2. 'De Wet F' exhibits a floriferous blooming habit.
3. 'De Wet F' exhibits a well-branched plant habit.

'De Wet F' can be compared to the cultivars 'Plepalila' (U.S. Plant Pat. No. 13,858) and 'Velvet Elvis' (U.S. Plant Pat. No. 25,020). 'Plepalila' is similar to 'De Wet F' in flower color. 'Plepalila' differs from 'De Wet F' in having petal lobes with distinct dark markings, less branching, smaller flowers, and in being less floriferous. 'Velvet Elvis' is similar to 'De Wet F' in having large purple flowers and a floriferous blooming habit. 'Velvet Elvis' differs from 'De Wet F' in having more elongated flower tubes and petals that are that are lavender in color with noticeable dark spots on the petals lobes.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

BRIEF DESCRIPTION OF THE DRAWINGS

The accompanying colored photographs illustrate the overall appearance and distinct characteristics of one year-old plants of the new *Plectranthus* as grown in a conventional greenhouse under natural light in a 9-cm containers in Boskoop, The Netherlands.

The photograph in FIG. 1 provides a side view of 'De Wet F' in bloom.

Figure 1:
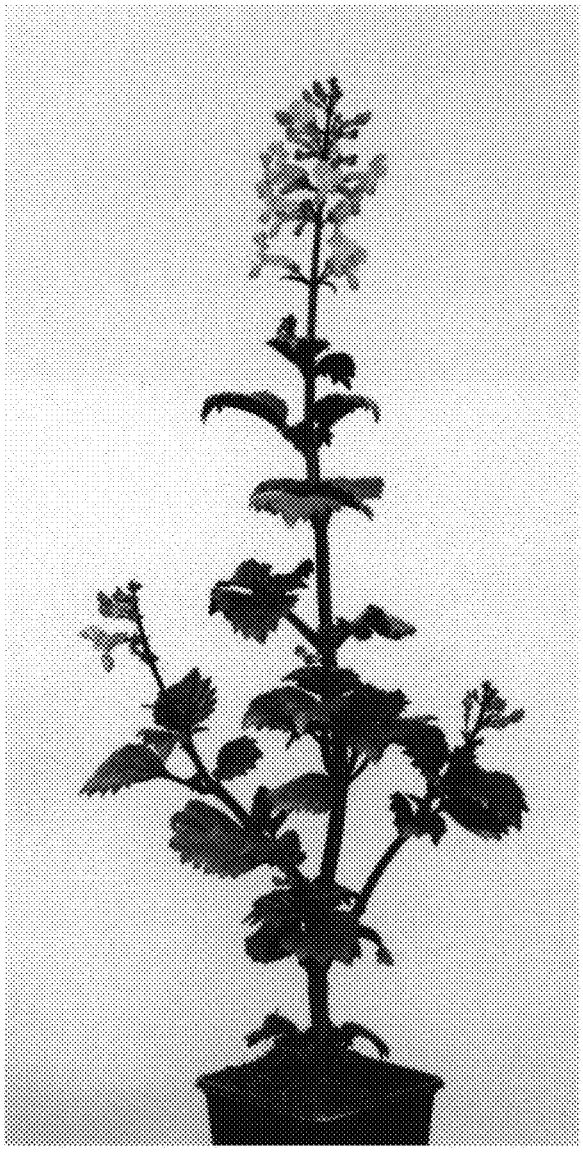
Figure 2:
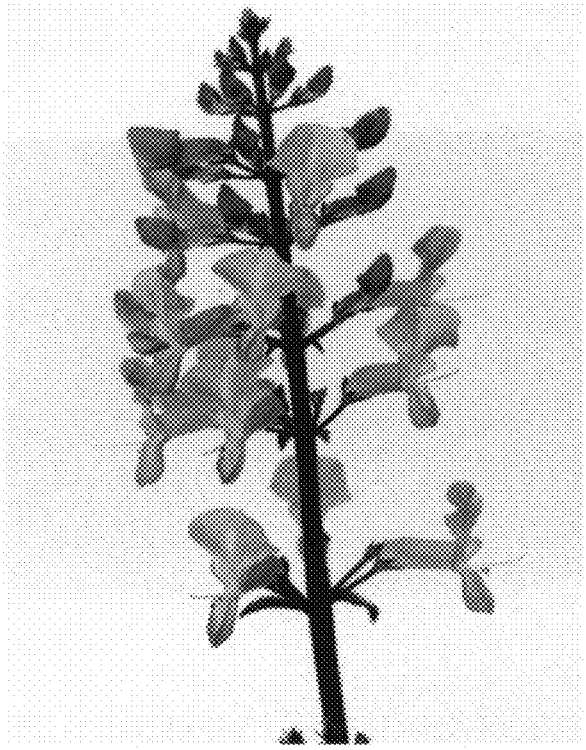

The photograph in FIG. 2 provides a close up view of an inflorescence of 'De Wet F'.

Figure 3:
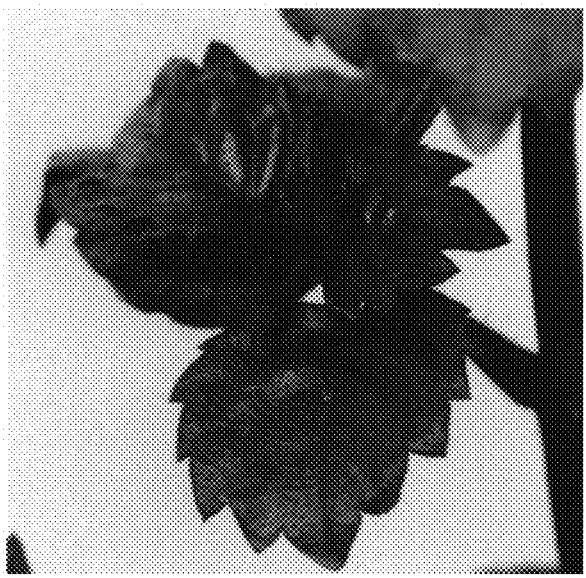

The photograph in FIG. 3. provides a close up view of the foliage of 'De Wet F'.

The colors in the photographs are as close as possible with the digital photography techniques utilized and the color values cited in the detailed botanical description accurately describe the colors of the new *Plectranthus*.

DETAILED BOTANICAL DESCRIPTION

The following is a detailed description of one year-old plants of the new cultivar as grown in a conventional greenhouse under natural light in 9-cm containers in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming habit.*—Blooms from mid summer to mid winter in South Africa.

*Plant type.*—Perennial, evergreen subshrub.

*Plant habit.*—Upright and well branched.

*Height and spread.*—Reaches about 70 cm in height and 60 cm in spread as a mature plant, average of 50 cm in height and 18 cm in width as grown in a 9-cm container.

*Cold hardiness.*—At least in U.S.D.A. Zone 10.

*Diseases and pests.*—No susceptibility or resistance to pests or diseases has been observed.

*Root description.*—Densely fibrous and freely branched.

*Root development.*—5 to 6 weeks to produce a rooted cutting and an average of 5 weeks to produce a young plant from a rooted cutting.

*Propagation*—Terminal stem cuttings.

*Growth rate.*—Moderate vigor.

Stem description:

*Stem shape.*—Quadrangular.

*Stem color.*—Young; a color between N186A and 200A, mature; 146A and strongly tinged with N186B (nodes and internodes).

*Stem surface.*—Young stems; sparse to moderate pubescence with hairs about 1 mm in length and a color between N186A and 200A, mature; glabrous and very slightly glossy.

*Stem size.*—Lateral branches; a average of 7.9 cm in length and 4.5 mm in diameter.

*Internode length.*—Average of 5.2 cm.

*Stem strength.*—Strong.

*Stem aspect.*—Upright.

*Branching.*—1 main stem and an average of 8 lateral branches per main stem.

*Stem fragrance.*—Somewhat mint-like when rubbed.

Foliage description:

*Leaf shape.*—Broad ovate to near orbicular.

*Leaf aspect.*—Slightly convex.

*Leaf division.*—Simple.

*Leaf base.*—Short Attenuate.

*Leaf apex.*—Acute.

*Leaf venation.*—Pinnate, upper surface 146A in color, lower surface a color between N186B and 200A.

*Leaf margins.*—Un-lobed, dentate.

*Leaf arrangement.*—Opposite.

*Leaf attachment.*—Petiolate.

*Leaf number.*—Average of 8 per lateral stem 7.8 cm in length.

*Leaf surface.*—Upper surface; moderatly glossy and moderately pubescent with soft hairs; about 1.25 mm in length and 187A in color, lower surface; slightly glossy and moderately pubescent with very short strigose soft hairs; about 0.5 mm in length and N187A in color, both surfaces slightly rugose.

*Leaf size.*—Average of 4.8 cm in length and 4.6 mm in width.

*Leaf color.*—Young and mature upper surface; NN137B, young and mature lower surface; a color between N186C and 200A.

*Leaf fragrance.*—Somewhat mint-like when rubbed, typical for *Plectranthus*.

*Petiole.*—An average of 2 cm in length and 2.5 mm in width, strong, color: upper surface a color between 146A and tinged with N186B, lower surface a color between N186A and 200A, surface on young petioles sparsely to moderately pubescent with soft hairs; 1 mm in length, a color between N186A and 200A, surface on mature petioles glossy and moderately glossy.

Inflorescence description:

*Inflorescence type.*—Axillary and terminal racemes.

*Inflorescence number.*—1 per main stem and lateral stems.

*Inflorescence fragrance.*—None.

*Lastingness of inflorescence.*—Flowers last an average of one week, self cleaning.

*Inflorescence size.*—Average of 11.6 cm in height and 6.8 cm in width.

*Flower buds.*—Average of 1.4 cm in length and 5 mm in diameter, oblong to slightly obovate in shape, moderately pubescent surface with very short hairs, color N81A with sepal portion 187C.

*Flowers.*—Single, held outward aspect, labiate in form, average of 2.8 cm in length (depth), 2.3 cm in in height (vertical) and 1.5 cm in diameter (horizontal) with throat diameter 2 mm in width, tube portion; 1.4 cm in length and 5 mm in diameter at widest part, average of 54 flowers per inflorescence (400 per plant).

*Petals.*—5; base fused into tube, 2 petals fused into one upper petal lobe, two lateral petal lobes and one lower petal lobe, upper petal lobe 1.1 cm in length and 1.5 cm in width, obcordate in shape, emarginate apex, color upper surface N82C to N82D and fading towards base 85D and lower surface N82B, lateral petal lobe 2.5 mm in length and 4 mm in width, reniform in shape, obtuse apex, color upper surface N82C in color and fading towards troat 85D and lower surface N82B, lower petal lobe 9 mm in length and 5 mm in width, folded orbicular in shape, broad acute apex, color upper surface N82C to N82D and fading towards base 85D and lower surface N82B, all margins entire with upper petal strongly undulate and other petals non-undulate, all petal lobe surfaces smooth, and slightly velvety and pubescent with very short glandular hairs 0.3 mm in length and N82A in color, tube; throat surface smooth and glabrous, outer surface moderately pubescent of very short glandular hairs 0.3 mm in length and N82A in color.

*Calyx.*—Flattened, 5 mm in length and 3 to 5 mm in width, comprised of 5 Sepals; rotate and fused at base, 2 lower sepals, 2 lateral sepals, 1 lower sepal, lower sepals; 5 mm in length, 1 mm in width, linear in shape, narrow acute apex, lateral sepals; 3 mm in length, 1 mm in width, linear in shape, narrow acute apex, upper sepal; 2 mm in length, 2.5 mm in width, ovate in shape, acute apex, all sepals; entire margins, color upper surfaces when opening and fully open 185D and tinged 146D with apex N186C, color lower surfaces when opening 187C, color lower surfaces when fully open 183C with veins 183A, surface upper surfaces smooth and glabrous, surface lower surface moderately pubescent with very short glandular hairs 0.2 mm in length (too fine to measure color reading).

*Peduncles.*—Moderatly strong, average of 11.3 cm in length and 3 mm in diameter, held at an angle of 0° to vertical for terminal inflorescence and 45° for axillary inflorescences, color between N186C and 200A, surface slightly glossy and moderately to densely covered with very short glandular hairs; 0.3 mm in length and a color between N186C and 200A.

*Pedicels.*—Moderately strong, average of 9 mm in length and 1 mm in diameter, held at a 65° angle to peduncle, a color between N186C and 200A (slightly darker), surface matt and moderately covered with very short glandular hairs; 0.3 mm in length and a color between N186C and 200A.

Reproductive organs:

*Pistils.*—1, pistil; 2.5 mm in length and 1 mm in diameter, stigma; 1 mm in diameter, cleft-shaped and 85B in color, style; 2.4 cm in length, 85D in color and fading at the base to N155A, ovary; 147D in color.

*Stamens.*—4, anthers; dorsifixed, short oblong in shape, average of 1 mm in length and 0.5 mm in width, darker than 83A in color, filament; 6 mm in length, N155A in color, pollen; low in quantity, 155A in color.

*Fruit and seeds.*—No fruit or seed development has been observed.

It is claimed:

1. A new and distinct cultivar of *Plectranthus* plant named 'De Wet F' as herein illustrated and described.

* * * * *